United States Patent [19]

Bartos et al.

[11] Patent Number: 4,863,853

[45] Date of Patent: Sep. 5, 1989

[54] METHOD OF DETERMINING THE DIAGNOSTIC VALUE OF MONITORING SERUM-CEA-LEVELS IN A CARCINOMA PATIENT UNDERGOING THERAPY

[75] Inventors: Dezsö S. Bartos, Solingen, Fed. Rep. of Germany; Denis Fitzpatrick, County Cork, Ireland

[73] Assignee: Bartos Patent Development and Holding Company Limited, Ireland

[21] Appl. No.: 484,995

[22] Filed: Apr. 14, 1983

[30] Foreign Application Priority Data

Apr. 21, 1982 [IE] Ireland ................................ 944/82

[51] Int. Cl.$^4$ ................. G01N 33/567; G01N 33/535
[52] U.S. Cl. ........................................ 435/7; 436/536; 436/542; 436/503; 436/504; 436/518
[58] Field of Search ............... 436/503, 504, 813, 542; 435/4, 7

[56] References Cited

U.S. PATENT DOCUMENTS

| | | | |
|---|---|---|---|
| 3,865,689 | 2/1975 | Goldenberg | 435/68 |
| 3,867,363 | 2/1975 | Hansen | 260/112 R |
| 3,956,258 | 5/1976 | Hansen | 260/112 R |
| 4,075,194 | 2/1978 | Sela et al. | 260/112.5 R |
| 4,086,217 | 4/1978 | Hansen | 260/112 R |
| 4,140,753 | 2/1979 | Edgington et al. | 424/1.1 |
| 4,145,336 | 3/1979 | Edgington et al. | 260/112 R |
| 4,152,410 | 5/1979 | Ishii | 424/1.1 |
| 4,180,499 | 12/1979 | Hansen | 260/112 R |
| 4,228,236 | 10/1980 | Jakstys et al. | 435/1 |
| 4,331,647 | 5/1982 | Goldenberg | 424/1.1 |
| 4,348,376 | 9/1982 | Goldenberg | 424/1.1 |
| 4,349,528 | 9/1982 | Koprowski et al. | 424/1.1 |
| 4,383,985 | 5/1983 | Bartorelli et al. | 424/1.1 |

OTHER PUBLICATIONS

Lamerz, R., et al., British Journal of Cancer, vol. 47, pp. 823–832, (1983).
Buchegger, F. et al., Journal of Immunological Methods, vol. 49, pp. 129–139, (1982).
Valdes, R. et al., Clinical Biochemistry, vol. 15, (5), pp. 241–247, (1982).
Buchegger, F. et al., Immunology Letters, vol. 5, pp. 85–91, (1982).
Fabricatorian, D. et al., Am. Clinical Biochemistry, vol. 18, pp. 248–251, (1981).
Von Kleist, S. et al., Arch. Geschwulstforsch., vol. 51, (6), pp. 523–526, (1981).
Yamashita, K. et al., Cancer Research, vol. 39, pp. 1760–1765, (1979).
Zimmerman, R., J. Immunological Methods, vol. 25, pp. 311–321, (1979).
Wahren, B., et al., Cancer, vol. 42, pp. 1870–1878, (1978).
Fujimoto, S. et al., Igaku No Ayumi, vol. III, (2), pp. 81–83, (1979), (English Abstract: See Chem. Abst. 92(7) 56502(g).
Kim Y. D., et al., Clinical Chemistry, vol. 25(5), pp. 773–776, (1979).

*Primary Examiner*—Margaret Moskowitz
*Attorney, Agent, or Firm*—Wegner & Bretschneider

[57] ABSTRACT

The diagnostic value of monitoring serum-CEA-levels in a patient undergoing therapy for a cancerous tumor is determined by obtaining cytosole from the tumor and quantitatively determining its CEA content. Preferably, the cytosole used is obtained from a portion of the tumor used for hormone receptor analysis.

3 Claims, 2 Drawing Sheets

METHOD OF DETERMINING THE DIAGNOSTIC VALUE OF MONITORING SERUM-CEA-LEVELS IN A CARCINOMA PATIENT UNDERGOING THERAPY

The invention relates to a test for predicting the use of carcino-embryonic-antigen (CEA) in carcinoma. The carcino-embryonic-antigen is both from the point of basic research and from the point of clinical use the most extensively studied substance from the group of tumor-markers. Its use in tumor screening, however, is not justified. Continual monitoring of CEA after primary therapy, however, is a valuable help in a number of kinds of tumors, both for therapy control and for the early detection of tumor regression.

The state of knowledge of CEA has been compiled in a series of papers at the Symposium: Carcinoembryonales Antigen und andere Tumormaker in Köln, November 1980 (1).

CEA has a particular value in mammacarcinoma. The associated problems can be seen in FIGS. 1 and 2 (FIG. 1).

Figure 1:
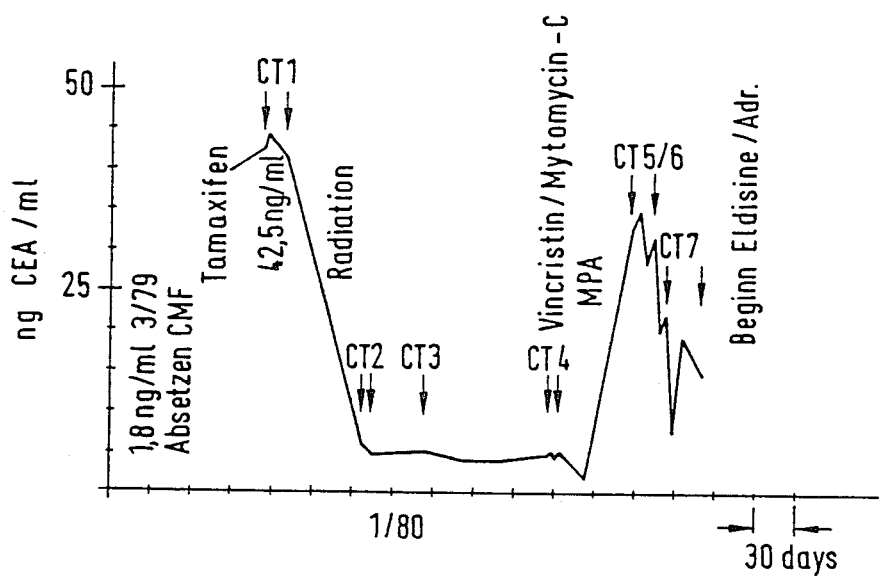
FIG. 1 is a serum-CEA-level progress curve of a patient with tissue-CEA-positive and CEA-secreting mammacarcinoma.

FIG. 1 shows the CEA-serum level course of a patient with metastasizing mammacarcinoma where the tumor progression is reflected in the CEA-values. This patient suffered in 1977 a diffuse locoregional regression; following introduction of chemo-therapy-combination with cyclophosphamide, methotrexate, 5-fluorouracil (CMF) a continuing full remission occurred. In March 1979 the chemotherapy was discontinued. The CEA-serum level was 1.8 nanogram per milliliter and lay in the normal range. 8½ months later a regression occurred which, in spite of the introduction of antioestrogen therapy with 2×10 mg tamoxifen daily, continued, the CEA-level continued to rise. A multiple bone metastasis occurred. After switching to chemo-therapy with adriblastin i-v-monotherapy with 30 mg/gm body surface area in combination with radiation a full clinical remission occurred. At CT 4 the adriblastin therapy was supplemented with 2 mg vincristin on the first day of the chemotherapy cycle ad also with 8 mg mytomycin-C daily in 5-hour continuous infusion over 5 days, in the hope, it would succeed, in substantially eliminating the tumor cells again and would bring the CEA-serum level back in the normal range. This proved to be misleading; a severe leucopenia occurred with an exponential progression, which inspite of high doses of gestagen therapy (daily 10×100 mg medroxyprogesteronacetate per os) could not be influenced. Only after renewed adriblastin chemotherapy with 50 mg i.v. (CT 5, 6, 7) could the progression be stopped and a renewed partial remission obtained.

It is obvious, that in this case of mammacarcinoma the CEA-measurement not only enabled the regression to be recognized early but as well made it possible to control the chemo-therapy and hormone therapy.

Figure 2:
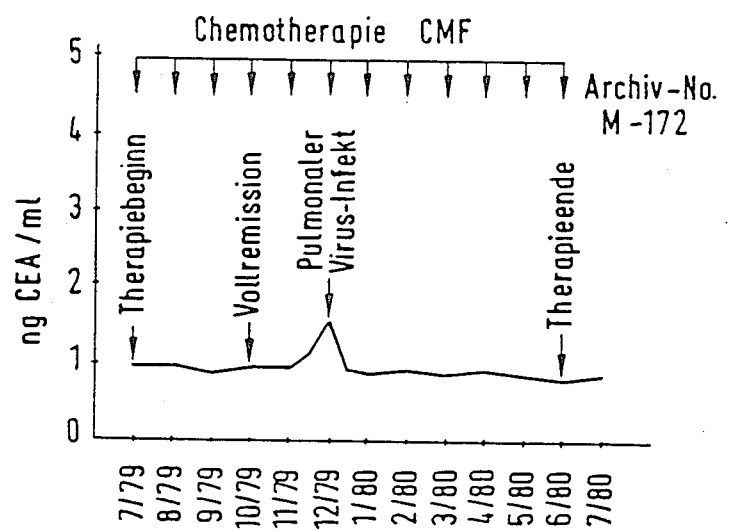
FIG. 2 is a serum-CEA-level progress curve of a patient with tissue-CEA-negative mammacarcinoma.

FIG. 2 shows likewise the CEA-course of a patient with metastasizing mammacarcinoma. The time span indicated corresponds with an extended local regional metastasis and the occurrence and maintenance of full remission with a chemo-therapy combination (CMF). From this figure one can draw the conclusion that in this case of mammacarcinoma a continuing CEA-measurement is completely pointless, because there is no relationship between the CEA-level and the clinical situation.

Figure 3A:
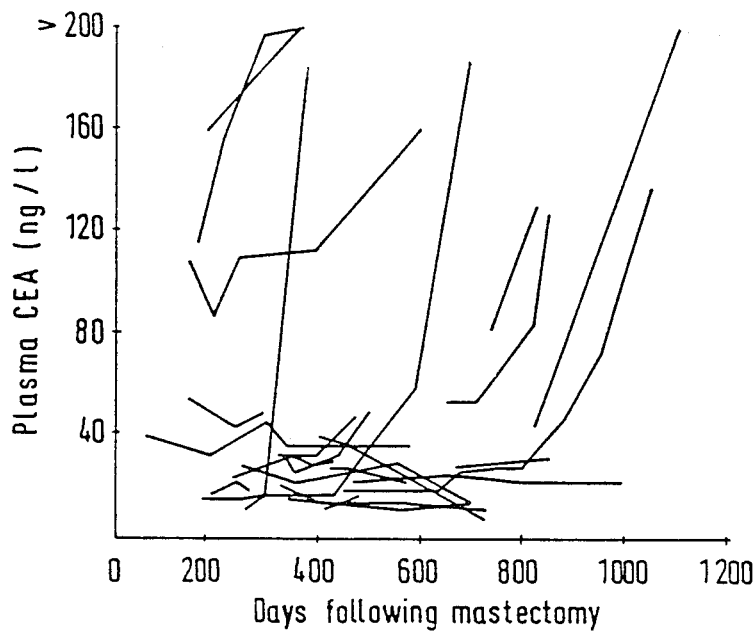
FIG. 3(a) is a plot of sequential plasma-CEA-levels in patients who have developed metastases.
Figure 3B:
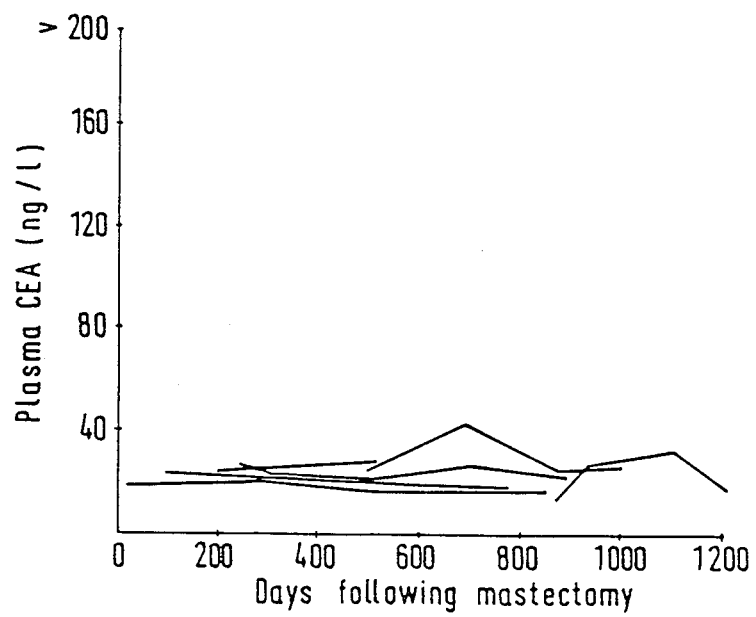
FIG. 3(b) is a plot of sequential plasma-CEA-levels in patients who remain disease free.

FIG. 3(2.) details the problem further: Only in a portion of mammacarcinoma cases where a regression or a tumor progression occurs does a significant rise in the serum or plasma CEA occur. It is only in these cases that a serial CEA-measurement is or would be meaningful for the early recognition of regression.

At the symposium (1) various authors came with differing methods to the conclusion, that at the time of a clinical-diagnostic determinable metastasis only about 43% of all mammacarcinoma cases had clearly exceeded the pathological cut-off value. This pathological cut-off value varies from manufacturer to producer. For example in the Abbott-EIA-CEA-test it is 5.0 nanogram CEA per milliliter serum. In the CEA-test of Hoffmann-La Roche this level is 2.5 nanogram CEA per milliliter. A further realization by the authors at the Symposium in Cologne was the discovery of a discrepancy between tissue-CEA-positivity and CEA-serum-positivity. In tissue in 70 to 90% of mammacarcinomas CEA can be detected by various methods, for example histochemical. On the other hand, we can only detect a measurable increase in the CEA level compared to the tumor-free state, either under or over the determined pathological cut-off value, in a considerably smaller percentage of metastising mammacarcinoma. This discrepancy was by a consensus so described that there existed CEA-negative and CEA-producing mammacarcinomas. Furthermore, we must distinguish in the case of CEA-producing mammacarcinomas between those which simply produce CEA and those which both produce and simultaneously secrete CEA. This assumption was further substantiated by extended work of D. Stefan Bartos and H. Bojar (3) by the immunofluorescent optical analysis of living isolated and cultivated mammacarcinomic cells with and without detection of the CEA-secretion.

A similar problem exists with many other types of tumor, for example bronchial carcinoma, so that this statement which was based on the example of breast cancer can be further generalized.

In the interest of cost effectiveness it is desirable and necessary to be able to make a prediction at the time of primary therapy as to in which cases of mammacarcinoma the monitoring of the CEA level is useful, in which cases would an early recognition of regression be possible and in which cases would the estimation of CEA only serve the purposes of follow up and documentation.

From the point of view of the patient it is important to know in advance whether with the help of a continuous monitoring of CEA in the follow-up period, a definitive statement can be made that a progression does not exist and that a growth of tumor can be excluded so that one can forgo invasive diagnostic, for example stintigraphy. It is clear that such a prediction can only be made in the knowledge of the tissue-CEA-values.

It can plainly be seen that perioperative analysis of the serum-CEA-level will not make this decision possible. It is true that in cases of multiple lymphnode attack and large primary tumors a definite drop in the serum-CEA-level in the postoperative period indicates a tissue-CEA-positivity and a CEA-secretion and that the CEA-measurement can be regarded as a tumor-marker, however, it can also be seen that this method will fail in the case of small tumors and cannot be recommended for routine use.

The method of D. Stefan Bartos and H. Bojar (3), which includes the isolation of living autologous tumor cells and the determination of CEA-secretion and the measurement of membrane CEA as well as a determination of the tumor cell distribution pattern of CEA, approximates to the ideal situation, but this integrated oncobiochemical immunological procedure can only be achieved routinely by the use of considerable resources.

Serial CEA-estimation for the early recognition of regression, for therapy control and therapy planning in mammacarcinoma is urgently desired in 20–25% of cases. In a further 15–20% of mammacarcinoma cases the CEA-estimation is within the limits of the additional technical laboratory requirements possible and recommended. In a further 10% of mammacarcinoma cases the CEA-estimation can fulfill an additional documentary role for scientific investigation. In the rest of the cases of mammacarcinoma (ca. 50%) CEA-estimation is completely meaningless.

There is therefore a requirement and an urgent necessity to be able to make a definitive statement on the applicability of the CEA-determinations in cases of mammacarcinoma as a tumor-marker, if possible at the time of primary therapy.

A decision on the positivity or negativity of tissue-CEA can be made with histochemical methods. This study can easily be carried out on archival paraffin sections. One can with this method sort out the tissue-CEA-negative mammacarcinoma, however, the procedure does not make possible a measurement of the extent of an increase in CEA in the course of the disease. It is not possible to determine whether the CEA-measurement is only suitable for documentary purposes or whether it makes possible an early detection of regression and a guidance of therapy in the case of such regression.

According to the invention there is provided a procedure for the prediction of the usefulness of CEA as a tumor-marker in carcinoma wherein the cytosole or tissue-CEA content of a tumor is determined as a means of predicting whether a serial CEA estimation would assist in the early recognition of regression would assist monitoring a therapy and/or therapy guidance.

In one embodiment of the invention the cytosole or tissue-CEA content is measured in parallel with a hormone receptor analysis. Preferably, the cytosole-CEA content is measured. Usually, the carcinoma is mamacarcinoma.

In one aspect the invention provides a procedure for the early prediction of the usefulness of the carcino-embryonic-antigen (CEA) as a tumor-marker in mammacarcinoma at the time of the primary therapy or at the time of analysis of a regression, wherein either in parallel to the obligatory hormone analysis, preferably from the cytosole which is obtained for this study or, with assistance of a similar quantitative tissue-CEA-estimation method, the cytosole or tissue CEA content is determined, and that based on this individual value and on the empirically determined cut-off value of these cytosole or tissue CEA content of many cases of the same tumor type with its distribution pattern in all cases related to the method of a particular reagent manufacture and considering empirical general knowledge of the occurrence and extent of tumor concordance of the CEA activity curve in mammacarcinoma related to the individual case of the individual patient, a decision is made or a prognosis is made as to whether in the individual tumor case a serial CEA-estimation would assist the early recognition of regression and/or would assist the monitoring a therapy and the therapy guidance and if so under which conditions and with what degree of confidence.

The invention further provides individual-CEA-estimation or continual-CEA-estimation in mammacarcinoma patients, wherein in order to obtain a better cost-effectiveness of the studies or a prediction with a higher information content a definite exclusion of a regression or a definite negation of a tumor progression in a concrete case is a prerequisite, wherein the person who carries out the test or the person who evaluates or interprets the test is made aware of the cytosole-CEA-content or the tissue-CEA-content of the tumor.

In one embodiment of the invention, the judgment of the results, the postoperative basal CEA-value of tumor-free stage before regression/progression are also measured or were measured and that this value is available or has been made available to the person responsible for evaluating the results.

In another embodiment of the invention, the cut-off value for a decision as to the suitability or un-suitability of the use of CEA as tumor-marker lies in a variable range which depends upon which cost/effectiveness-relationship has been chosen.

The invention also provides a procedure for the prediction of the usefulness of the carcino-embryonalic-antigen (CEA) as a tumor-marker in tumor forms other than mammacarcinoma, preferably for example brochial carcinoma, ovarial carcinoma, bladder and kidney carcinoma etc., wherein one uses the same procedural technical methods that have been described for mammacarcinoma.

The invention particularly provides for the communication of a quantitative cytosole or tissue CEA content value by a laboratory or an employee to the user or to the patients themselves.

The object of this invention therefore is process for testing the usefulness of the carcino-embryonic-antigen (CEA) as tumor-marker in serum at the time of the primary therapy or at the time of analysis of a regression, characterized in that the CEA content is determined quantitatively in cytosole or tissue of the tumor. A further object is a process according to claim 1, characterized in that the CEA content is determined quantitatively in a cytosole which is obtained from the tumor for the hormone receptor analysis. The invention will be more clearly understood from the following description, given by way of example only. We suggest integrating the quantitative tissue-CEA-measurement with the hormone-receptor-analysis and that on the basis of a cytosole-CEA-measurement. The hormone-receptor-analysis is an established predictive analysis method (4) that indicates the possibility of an effective hormone therapy in cases of mammacarcinoma with a high success rate. In fact Nagel (4) has demanded that hormone-receptor analysis should be carried out routinely on all mammacarcinoma patients at the time of primary therapy. The establishment of corresponding laboratory capacities has started and already the rate of receptor analysis has exceeded 50% in the U.S.A. For this purpose organizational structures are being established. For this reason, the question described above whether to use cytosole estimation or not must be answered. The combination of cytosole-CEA-estimation with hormone receptor analysis allows a considerable rationalization and a considerable cost saving. It is not necessary to send tumor tissue to a second laboratory. Smaller amounts of tumor material are required, which is an advantage in the case of small tumors. Cytosole for hormone-receptor-analysis is routinely prepared. Furthermore, it is necessary to determine the cytosole protein content accurately for the quantification of the hormone receptor concentration. This requires a not inconsiderable amount of preparation. It is possible therefore to similarly express the cytosole-CEA-concentration in nanograms per milligram cytosole protein. The new procedure is as hereunder described.

I. Material and Method of the Cytosole-CEA-Estimation

For the cytosole-CEA-estimation the same cytosole is preferably used that is available for the preparation of hormone receptor analysis. Tumor tissue delivered deep-frozen or stored temporarily frozen is freed from fat and connective tissue in frozen condition and cooled firstly to $-170°$ C. with liquid nitrogen in a stainless steel container of a dysmembrator apparatus (firm B. Braun, Apparatebau, Melsungen), then made smaller coarsely with a steel hammer and finally pulverized in the dysmembrator with the assistance of steel bearings. The powdered deep-frozen tumor tissue so obtained is extracted in cooled state with gentle shaking for 15 to 20 minutes with a two- to fivefold amount of 0.15M PBS (phosphate buffered saline). Finally the non-solvable cell particles are removed by centrifugation at 30,000 G for 45 minutes in a refrigerated centrifuge (Beckmann type). The supernatant forms the cytosol fraction that is then routinely analyzed for hormone receptors.

The cytosole-CEA-estimation is carried out on the cytosole which is stored in the meantime in a deep-frozen state (under $-21°$ C.). 100 microliter of cytosole are mixed with 200 microliters 0.2 ml sodium-acetate-Buffer-ph 5.0 and heated at $70°$ C. in a water bath for 15 minutes. This precipitates the protein content of the cytosole. The CEA, however, remains almost quantitatively (98% or more) in the supernatant. After centrifugation in a standard laboratory centrifuge for 15 minutes at 1500 G the CEA in the supernatant is measured, in the present study with the use of an Abbott-CEA-enzymimmunoassay. If cytosole-CEA-concentrations greater than 60 nanogram/ml are found, then the sample is further diluted in PBS 1:10 and CEA again determined. Further dilutions have so far not been necessary in cases of mammacarcinoma (N=311). In order to qualify the cytosole-CEA-content the corrected protein factor from the hormone receptor analysis is used. Hormone receptor concentrations are measured and expressed in femtomol/mg cytosole protein. For this purpose the total protein content of the cytosole prepared as above is determined with a suitable method, e.g. total protein content after Lowry. Further, albumin concentration of the cytosole preparation is determined with a suitable standardized immunochemical method, e.g. the radial immunodiffusion after Mancini (partigen-albumin-plates, Behringwerke AG, Marburg). Human albumin is only produced in the liver and does not occur within the cells. Using a factor based on the two protein values it is possible to determine exactly the intracellular protein content or cytosole protein content of the individual tumor samples and to express it in mg/ml of prepared cytosole. The cytosole-CEA-content that is measured in the prepared cytosole is expressed as nanogram CEA per milligram cytosole protein. This cytosole-CEA-value is then used to determine the suitability of CEA as a tumor-marker in the corresponding patient.

This procedure rationalizes optimally the quantification of tissue-CEA.

Table 1 shows a representative distribution (N=311) of cytosole-CEA-content of mammacarcinomas based on the described procedures and the CEA-reagents used. Abbott-CEA-EIA-reagents are produced using CEA isolated from permanent tumor cell cultures. This allows an extensive standarization and stability of the determined values to be assured. This is a pre-condition that the already mentioned predictions can be regarded as a valid prediction (predictive test).

If one wants to use reagents from a different source, then in the absence of a standardized CEA measurement it is necessary to proceed in a similar manner. First of all one must establish a representative distribution pattern of the tissue-CEA-distribution pattern of a particular form of tumor based on a large number of cytosole CEA or tissue CEA estimations.

II. Reproducibility of the Cytosole-CEA-Estimation

From table 2 the results of parallel estimations can be seen. In the years 1978–1981 not only the serum sample of patients of the St. Lukas-Klinik, Solingen, were archived but also deep-frozen tumor tissue, insofar as this was available in sufficient quantity. These tissues were originally stored at $-70°$ C. for up to 46 months with the original intention of preparing antigen. In the meantime, however, advances in the research of mammacarcinoma immunology were achieved which made it more relevant to use the living isolated autologous tumor cells. For this reason the stored tumor samples were again retrospectively worked up for the preparations of cytosole. In this way for the period 11/80 to 12/81 duplicate estimations were estimation from the same tumor samples were carried out by two different workers on two different days. The results in table 2 show an excellent reproducibility of the cytosole-CEA-estimation.

III. Cytosole-CEA-Estimation from Primary Tumors and Lymphnode Metastases

Table 3 shows some results. From this it can be seen that between the cytosole CEA content of the primary tumor and the lymphnode metastases deviations can readily occur, whereby clinical relevance can be assigned to the metastasing tissue. This corresponds with other observations (5).

Immunohistochemically the CEA-content in tissue of lymphnode metastases in mammacarcinoma is more often higher compared to the primary tumor. This phenomenon has also been observed by the authors D. Stefan Bartos and H. Bojar (3). The secretion of CEA or the demonstration of membrane-containing CEA in living isolated mammacarcinoma cases occurs to a lesser extent in the lymphnode metastasing cells compared to the cells of the primary tumor. On the other hand, the cytosole-CEA-content of these cells is higher after arresting the CEA secretion capability as a sign of further differentiation, loss of cell performance. As in the case of the hormone receptor analysis one should, in the case of lymphnode metastases, as well as the receptor analysis do the cytosole-CEA-estimation in duplicate and allow for these values when making decisions.

IV. Transformation of the Cytosole-CEA-Value into a Predictive Test by Comparison of these values with the course of the CEA-concentration of patients from the Solingen Mammatumorserumpanell The raw data of the cytosole-CEA-estimations can be seen in table 1.

With support of the Serobac-Institute for Onkology and the firm Bartos-Patent Development & Holding Company Ltd. all mammacarcinoma patients of the St. Lukas-Klinik, Solingen, from the second 1978 to the 12th 1981 as well as further mammacarcinoma patients from hospitals in Dublin systematic serum samples were collected and divided into smaller lots and stored frozen at $-28°$ C. From each mammacarcinoma patient both a pre- and post-operative serum sample was frozen. In addition if chemotherapy or hormone adjuvant therapy was carried out, further serial serum frozen. In the same way patients with metastasizing mammacarcinoma before beginning therapy, in full remission state, and in the case of further growth of tumor were similarly studied. In the meantime the data from the results of a total of 8456 CEA-estimations with the corresponding clinical picture from a total of 831 treated patients (294 treated primary mammcarcinoma) are available.

This data material makes it possible to determine the limit of highest unspecific CEA serum level changes, which are not caused by the tumor and which were registered during the course of the study up to 4 years. The highest non-tumor-specific gram/ml serum (Abbott-CEA-EIA) or 1.5 nanogram CEA/ml serum compared with the postoperative basal CEA-value or the value that could be measured in an extended tumor state and the full remission or complete freedom from tumor. If one compares the determined cytosole-CEA-value and the measured change in the serum-CEA-level with preoperative/postoperative or postoperative and the state of extended metastases following a regression or the state of extended metastases and the stadium of full remission, one comes to the conclusions that by using the Abbott-CEA-RIA-test or the Abbott-CEA-EIA-test continual estimations in cases of mammacarcinoma.

(1) Tumors with a cytosole-CEA-content greater than 20 to 30 nanogram/mg cytosole protein are suitable for early recognition of regression ($=20$ to 25% of the cut-off level of the cytosole or tissue-CEA-estimation method). The possibility of therapy and progression control in these tumors with cytosole-CEA-content is obvious.

(2) Tumors with a cytosole-CEA-content from 10 to 20 nanogram/mg cytosole protein ($=$up to 35% of the significant or cut-off value of a cytosole-CEA- or tissue-CEA-estimation), in these cases a progression or therapy control as well as a therapy and an alteration of therapy with the assistance of the CEA-estimation is possible and recommended, if the technical laboratory provisions are complied with. The laboratory provisions are that the old previous serum samples are stored preferably at $-21°$ C and that the last serum sample is always run with new samples in a series. This procedure is based on the comparison of reproducibility of measurements on the day (intraassay reproducibility) compared to the reproducibility from day to day (interassay reproducibility). It is quite clear that measurements carried out in a series on the same day achieve a higher precision and therefore the tumor-marker can be used down to a lower tissue-concentration.

(3) CEA-estimation in mammacarcinoma with a cytosole-CEA-content down to 5 nanogram/mg cytosole protein (45% of the cut-off value of a cytosole or tissue CEA estimation procedure) can be used for scientific studies and for documentary purposes when the technical laboratory provisions of the previous point are maintained.

(4) CEA-estimations in mammacarcinoma and a cytosole-CEA-content less than 5 nanogram of CEA per milligram of Cytosole protein (over 45% of the cut-off value of a cytosole or tissue CEA estimation method) are completely meaningless even when in the final stage of the disease a measurable increase in the serum-CEA-level in a higher percentage than said cut-off values occurs. This occurs so late that the CEA-estimation is without practical value and is pointless.

It should be pointed out that these projections or discriminations in the planning of therapeutic concepts which are based on anti-CEA-antibody-containing immunotherapeutics in mammacarcinoma cannot be used. No optimal projection can be made on the CEA secretion capability or the existence in membrane of CEA-molecules which are necessary for immunotherapy with anti-CEA-antibodies, if the tumor cells are to be reached, and therefore cannot be based optimal on a cytosole-CEA- or tis- sue-CEA-estimation which give a statical probability value only. For the exact determination, the isolation and analysis of autologous living tumor cells is necessary.

TABLE 1

Cytosole-CEA-distribution pattern in mammacarcinoma determined with Abbott-CEA-EIA Highest measured Cytosole-CEA-value: 153 nanogram of CEA per milligram Cytosole protein.

Results of the evaluation of empirical experience over 48 months from a total of 8456 CEA-estimations in 831 mammatumor patients, 294 of them had primary treated mammacarcinoma:

Continuing CEA-estimation in mammatumors with a cytosole-CEA-content greater than 20 nanograms per milligram cytosole protein are indicated. Apart from a progression and therapy control regression can be detected earlier.

In mammatumors with a cytosole-CEA-content between 10 and 20 nanogram CEA per milligram cytosole protein the continuing CEA-estimations are useful meaningful when the corresponding technical laboratory provisions are complied with (see text). Therapy and progression control is possible.

In mammatumors with a cytosole-CEA-content between 5 to 10 nanogram per milligram cytosole protein the CEA-estimation serves as a documentary purposes when the corresponding technical laboratory provisions are complied with.

CEA-estimation in mammacarcinoma with a CEA-content of less than 5 nanogram per milligram cytosole protein are completely meaningless.

TABLE 2

Results of the duplicate cytosole-CEA-estimations in mammacarcinoma from the same tumor.

| Sample-No.: | 1st Estimation | 2nd Estimation | |
|---|---|---|---|
| 1. | 0,53 | 1,1 | nanogram CEA/mg cytosole protein |
| 2. | 0,06 | 0,09 | " |
| 3. | 20,7 | 23,5 | " |
| 4. | 15,52 | 20,68 | " |
| 5. | 1,05 | 1,8 | " |
| 6. | 25,54 | 21,5 | " |
| 7. | 0,25 | 1,8 | " |
| 8. | 5,94 | 8,44 | " |
| 9. | 1,47 | 0,06 | " |
| 10. | 2,70 | 0,08 | " |
| 11. | 0,53 | 0,53 | " |
| 12. | 101,00 | 138,00 | " |
| 13. | 1,16 | 1,05 | " |
| 14. | 0,45 | 1,28 | " |
| 15. | 25,50 | 23,4 | " |
| 16. | 0,04 | 1,8 | " |

TABLE 3

Results of the cytosole-CEA-estimation in mammacarcinoma from the primary tumor and the LK-metastase

| Sample-No.: | Cytosol-CEA | in the primary tumor/ in LK metastases |
|---|---|---|
| 1. | nanogram CEA/mg cytosole protein | 1,05/1,8 |
| 2. | " | 5,03/18,5 |
| 3. | " | 25,54/28,3 |
| 4. | " | 0,45/0,94 |
| 5. | " | 0,25/0,51 |
| 6. | " | 19,25/23,5 |
| 7. | " | 0,20/0,15 |
| 8. | " | 1,85/4,8 |
| 9. | " | 12,6/25,0 |

Literature:

1. G. Uhlenbruck und G. Wintzer: CEA/Carcinoembryonales Antigen und andere Tumormarker. Ein Symposiumsband/Tumordiagnostik Verlag D-7250 Leonberg 1981.
2. R. C. Coombes et al.: Carcinoembryonic Antigen Estaminations Aid to the Management of Breast Carcinoma. Seite 148 bis 160 in G. Uhlenbruck und G. Wintzer: CEA/Tarcinoembraonales Antigen und andere Tumormarker. Ein Symposiumsband/Tumordiagnostik Verlag D-7250 Leonberg 1981.
3. D. Stefan Bartos und H. Bojar: Das Carcinoembryonales Antigen und das Mammakarzinom aus onkobiochemischer Sicht. Publikation in Vorbereitung.
4. G. A. Nagel und H. E. Wander: Metastasierende Mammakazinome. Therapieplanung unter Berücksichtigung von Prognosefaktoren, Dt. Ärzteblatt 9, 399 (1981)

The invention is not limited to the procedure hereinbefore described which may be varied in detail.

We claim:

1. A method for establishing the diagnostic value of monitoring serum-CEA levels in a patient undergoing therapy for a tumor selected from the group consisting of mammacarcinoma, bronchial carcinoma, ovarian carcinoma, bladder carcinoma and kidney carcinoma, which comprises excising a portion of said tumor from said patient, obtaining cytosol from the excised portion of said tumor, quantitatively assaying the excised tumor CEA content to evaluate CEA content per total protein content in the cytosol and determining whether such content is greater than a cutoff value of an empirically found distribution pattern of CEA content per total protein content in cytosol.

2. A method according to claim 1, wherein serum-CEA levels are monitored as indicia of tumor remission or relapse.

3. A method according to claim 1, wherein the tumor is mammacarcinoma.

* * * * *